United States Patent
Zhang et al.

(10) Patent No.: US 10,053,531 B2
(45) Date of Patent: Aug. 21, 2018

(54) MOLECULARLY IMPRINTED POLYMER NANOPARTICLES COMPATIBLE WITH BIOLOGICAL SAMPLES AND PREPARATION METHOD THEREOF

(71) Applicant: Nankai University, Tianjin (CN)

(72) Inventors: Huiqi Zhang, Tianjin (CN); Yue Ma, Tianjin (CN); Ying Zhang, Tianjin (CN); Guoqing Pan, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 328 days.

(21) Appl. No.: 14/646,180

(22) PCT Filed: Nov. 20, 2013

(86) PCT No.: PCT/CN2013/087538
§ 371 (c)(1),
(2) Date: May 20, 2015

(87) PCT Pub. No.: WO2014/079367
PCT Pub. Date: May 30, 2014

(65) Prior Publication Data
US 2015/0299366 A1 Oct. 22, 2015

(30) Foreign Application Priority Data
Nov. 20, 2012 (CN) .......................... 2012 1 0470277

(51) Int. Cl.
*C08F 267/06* (2006.01)
*G01N 33/543* (2006.01)
(Continued)

(52) U.S. Cl.
CPC .............. *C08F 267/06* (2013.01); *C08F 2/38* (2013.01); *C08F 220/06* (2013.01);
(Continued)

(58) Field of Classification Search
None
See application file for complete search history.

(56) References Cited

U.S. PATENT DOCUMENTS

2009/0197297 A1  8/2009  Murray et al.

FOREIGN PATENT DOCUMENTS

| CN | 1673216 A | 9/2005 |
|---|---|---|
| CN | 102059104 A | 5/2011 |
| CN | 102952236 A | 3/2013 |

OTHER PUBLICATIONS

Office Action issued by the Chinese Patent Office dated Apr. 5, 2017 in related Application No. 201210470277.1.
(Continued)

*Primary Examiner* — Ronak Patel
(74) *Attorney, Agent, or Firm* — Gesmer Updegrove LLP (57) ABSTRACT

This invention provides molecularly imprinted polymer nanoparticles compatible with biological samples, and in particular pure biological samples and a preparation method thereof. Said molecularly imprinted polymer nanoparticles have a crosslinking degree exceeding 50%, a particle diameter of 10 to 500 nm, hydrophilic polymer brushes on its surfaces and can be prepared by introducing appropriate hydrophilic macromolecular chain transfer agents into reversible addition-fragmentation chain transfer (RAFT) precipitation polymerization systems through the one-pot synthesis. The preparation method is simple, features a broad range of application and yields a pure product. The obtained hydrophilic molecularly imprinted polymer nanoparticles have prospects for a wide range of application in biological sample analysis, medical clinical immune analysis, food and environmental monitoring, biomimetic sensors, etc.

16 Claims, 4 Drawing Sheets

(CTA refers to chain transfer agent and macro-CTA refers to macromolecular CTA)

(51) Int. Cl.
  *C08F 2/38* (2006.01)
  *C08F 220/06* (2006.01)
  *C08F 222/14* (2006.01)
  *C08F 226/06* (2006.01)
(52) U.S. Cl.
  CPC .......... *C08F 222/14* (2013.01); *C08F 226/06* (2013.01); *G01N 33/54346* (2013.01); *C08F 2438/03* (2013.01); *G01N 2600/00* (2013.01)

(56) References Cited

OTHER PUBLICATIONS

Ma, Yue et al. Narowly Dispersed Hydrophilic Molecularly Imprinted Polymer Nanoparticles for Efficient Molecular Recognition in real Aqueous Samples Including River Water, Milk, and Bovine Serum. Angewandte Chemie International Edition, Jan. 28, 2013, vol. 52, No. 5., pp. 1511-1514.
Ma, Yue et al. Effiem Symhesis of Narowly Dispersed Molecularly Imprinted Polymer Microspheres with Multiple Stilnuli-Responsive Template Binding Propemes in Aqueous Media. Chemical Communications. Jun. 25, 2012, vol. 48, No. 50., pp. 6217-6219.
Pan, Guoqing et al. Efficient One-Pot Synthesis of Water-Compatible Molecularly Imprinted Polymer Microspheres by Facile RAFT Precipitation Polymerization. Angewandte Chemie International Edition, Dec. 2, 2011, vol. 50, No. 49., pp. 11731-11734.
International Search Report issues in PCT/CN2013/087538 dated Mar. 20, 2014.
Written Opinion issued in PCT/CN2013/087538 dated Mar. 20, 2014.

(CTA refers to chain transfer agent and macro-CTA refers to macromolecular CTA)

MOLECULARLY IMPRINTED POLYMER NANOPARTICLES COMPATIBLE WITH BIOLOGICAL SAMPLES AND PREPARATION METHOD THEREOF

PRIORITY INFORMATION

This application is a 371 of PCT Application No. PCT/CN2013/087538 filed Nov. 20, 2013, which claims priority to Chinese Patent Application No. 201210470277.1 filed Nov. 20, 2012, both of which are incorporated herein by reference in their entireties.

TECHNICAL FIELD

The present invention relates to molecularly imprinted polymer nanoparticles and a preparation method thereof, and it especially relates to molecularly imprinted polymer nanoparticles with excellent molecular recognition ability toward small organic molecules in biological samples, and in particular pure biological samples, and a preparation method thereof. To be specific, the present invention relates to molecularly imprinted polymer nanoparticles with surface-grafted hydrophilic polymer brushes and their one-pot preparation method.

BACKGROUND ART

In nature, the molecular recognition based on biological receptors (such as enzymes, antibodies, etc.) plays a decisive role in most biological processes (such as immune responses, ligand-receptor interaction, and enzyme catalysis). How to develop synthetic receptors with an affinity and specificity approaching those of biological receptors has been a significant challenge for the contemporary chemists. So far, many low molecular weight organic receptors have been prepared (F. Hof, S. L. Craig, C. Nuckolls, J. Rebek Jr., *Angew. Chem. Int. Ed.* 2002, 41, 1488-1508; D. M. Vriezema, M. C. Aragonés, J. A. A. W. Elemans, J. J. L. M. Cornelissen, A. E. Rowan, R. J. M. Nolte, *Chem. Rev.* 2005, 105, 1445-1490). The construction of such synthetic receptors, however, usually requires complicated multi-step synthesis, which severely limits their broad applications. Developing other synthetically more accessible receptors has become a hot research topic in recent years.

Molecular imprinting technique is a facile and efficient new method to prepare polymer receptors with specific molecular recognition sites (H. Zhang, L. Ye, K. Mosbach, *J. Mol. Recognit.* 2006, 19, 248-259). The molecularly imprinted polymers (simply MIPs) generated by this technique have attracted enormous attention due to their high specific molecular recognition ability, ease of preparation, and good thermal and chemical stability. In the present, molecular imprinting technique has become a straightforward and efficient way to obtaining biomimetic synthetic receptors. One of the most distinct characteristics of the molecular imprinting process is its generality, which offers the freedom to prepare MIPs for a wide range of templates without appreciably changing the synthetic protocols. So far, the application studies of the MIPs have been extended to many areas, including chromatographic stationary-phase, solid-phase extraction, immunoassays, biomimetic sensors, artificial enzymes, organic synthesis, and drug delivery. They have shown great potential for applications in the fields of food safety and environmental monitoring. The ultimate goal of the molecular imprinting study is to generate MIPs that are comparable with biological receptors, which can eventually replace the biological receptors in practical applications.

Despite the fact that significant progress has been achieved in the molecular imprinting field and some MIPs have become commercially available for some specific applications (e.g., solid-phase extraction), there still exist some key problems and challenges in this area, which significantly limits their broad practical applications. One of such challenges is how to prepare MIPs with excellent specific recognition ability toward small organic analytes (most of the environmental pollutants, drugs, antibiotics, pesticides, and herbicides are small organic molecules) in aqueous media. The previously developed MIPs that target small organic molecules normally only show good molecular recognition ability in organic solvents, and those truly compatible with aqueous samples are rather rare. It is, however, certainly worth replacing organic solvents with water from the viewpoint of many aspects such as economy, ecology, and environmental protection. In addition, it is definitely necessary to use water as the solvent for the potential application of the MIPs in the field of biotechnology. Furthermore, the use of MIPs capable of efficient molecular recognition in aqueous media can help achieve the goal of direct and rapid sensing of small organic analytes in their practical applications in such areas as environmental and food monitoring and clinical diagnostics. Although some advances have been made in this aspect by using specifically designed functional monomers (G. Wulff, R. Schöonfeld, *Adv. Mater* 1998, 10, 957-959; H. Asanuma, T. Hishiya, M. Komiyama, *Adv. Mater* 2000, 12, 1019-1030; P. Manesiotis, A. J. Hall, J. Courtois, K. Irgum, B. Sellergren, *Angew. Chem. Int. Ed.* 2005, 44, 3902-3906; J. L. Urraca, A. J. Hall, M. C. Moreno-Bondi, B. Sellergren, *Angew. Chem. Int. Ed.* 2006, 45, 5158-5161), by using traditional molecular imprinting method (L. I. Anderson, R. Müller, G. Vlatakis, K. Mosbach, *Proc. Natl. Acad. Sci. U.S.A.* 1995, 92, 4788-4792; J. G. Karlsson, L. I. Andersson, I. A. Nicholls, *Anal. Chim. Acta* 2001, 435, 57-64), or by adding hydrophilic co-monomers into the molecular imprinting systems (B. Dirion, Z. Cobb, E. Schillinger, L. I. Andersson, B. Sellergren, *J. Am. Chem. Soc.* 2003, 125, 15101-15109), the preparation of MIPs compatible with pure biological samples remains a challenging task in the present.

It is well known that biological samples, and in particular pure biological samples, have rather complex components (for example, biological samples such as milk and serum contain a large amount of proteins), which makes it very difficult for the MIPs to specifically recognize small organic analytes in real biological samples. It is noted that although there have been many reports on the application of MIPs as solid-phase extraction materials for the separation of target analytes in real biological matrices (B. Sellergren, *Anal. Chem.* 1994, 66, 1578-1582; E. Caro, R. M. Marcé, F. Borrull, P. A. G. Cormack, D. C. Sherrington, *Trend. Anal. Chem.* 2006, 25, 143-154; B. Tse Sum Bui, K. Haupt, *Anal. Bioanal. Chem.* 2010, 398, 2481-2492; E. Turiel, A. Martín-Esteban, *Anal. Chim. Acta* 2010, 668, 87-99), however, the selectivity of the MIPs in this case is mainly controlled by the washing solvents used in the extraction processes. This is much easier than the direct use of MIPs for the molecular recognition in real matrices, as the latter case is mainly fixed by the nature of MIPs (V. Pichon, F. Chapuis-Hugon, *Anal. Chim. Acta* 2008, 622, 48-61).

Recently, the inventors reported the one-pot synthesis of pure water-compatible MIP microspheres with surface-grafted hydrophilic polymer brushes through the introduction of hydrophilic macromolecular chain transfer agents into the reversible addition-fragmentation chain transfer (RAFT) precipitation polymerization system (G. Pan, Y. Zhang, Y. Ma, C. Li, H. Zhang, *Angew. Chem. Int. Ed.* 2011, 50, 11731-11734). The MIP particles prepared by the above method, however, are of micrometer sizes, and in spite of their compatibility with normal aqueous samples, they cannot be used for the direct analyses of biological samples because of the significant adsorption of proteins in biological samples onto the surfaces of the MIP microspheres. Therefore, the inventors successfully prepared MIP nanoparticles with surface-grafted hydrophilic polymer brushes that are compatible with biological samples, and in particular pure biological samples in a one-pot method on the basis of the above work. The nanosized volumes imparted these hydrophilic MIP nanoparticles with excellent water dispersion stability, which paved the way for their applications in such areas as environmental monitoring, food safety, and clinical diagnostics.

SUMMARY OF THE INVENTION

The present invention aims to provide MIP nanoparticles compatible with biological samples, and in particular pure biological samples, and a preparation method thereof, in order to compensate for the defects of the existing technology and lay the foundation for the practical applications of the MIPs by their eventual replacement of natural receptors.

According to the concept of the present invention, MIP nanoparticles with surface-grafted hydrophilic polymer brushes and thus MIPs compatible with pure biological samples can be obtained by introducing appropriate hydrophilic macromolecular chain transfer agents into RAFT precipitation polymerization systems through the one-pot synthesis.

The detailed synthetic procedure of the present invention is described as follows:

(1) Dissolving the template molecule, functional monomer, and crosslinker into an appropriate solvent with their molar ratio being 1:1~10:4~80 and the volume percentage of the functional monomer and crosslinker in the whole reaction system being 0.5~10%.

(2) Adding the initiator that is 0.5~10% relative to the total amount of the functional monomer and crosslinker and appropriate amount of the chain transfer agent into the polymerization system, wherein the molar ratio of the initiator to chain transfer agent is 1:1~20.

(3) The used chain transfer agent includes a small chain transfer agent and a hydrophilic macromolecular chain transfer agent, wherein the molar percentage of the small chain transfer agent is 0~95%.

(4) After the complete dissolution of all the above reactants, the reaction mixture is degassed by being purged with argon or nitrogen for 5~60 min to remove oxygen from the polymerization system, sealed, and then immersed into an oil bath with a temperature of 25~100° C. and the polymerization is allowed to take place for 1~100 h. After the ultrasonication of the reaction mixture for 5~30 min, the polymer nanoparticles with entrapped template molecules are collected by high speed centrifugation.

(5) The resulting polymer nanoparticles are then washed with methanol/acetic acid (with a volume ratio of 10/0.1~10/10) for 12~72 h and methanol for 12~48 h successively until no template molecules can be detected in the washing solution. After being dried at 20~60° C. under vacuum to the constant weight, MIP nanoparticles with surface-grafted hydrophilic polymer brushes are obtained.

Said functional monomer is 4-vinylpyridine, 2-vinylpyridine, 4-vinylbenzoic acid, (meth)acrylic acid, trifluoromethyl acrylic acid, 2-hydroxyethyl methylacrylate, dimethylaminoethyl methacrylate, (meth)acrylamide, 2-acrylamido-2-methyl-1-propanesulfonic acid, 4-vinylimidazole, itaconic acid or N-vinylpyrrolidone.

Said crosslinker is ethylene glycol dimethacrylate, trimethylolpropane trimethacrylate, pentaerythritol triacrylate, divinylbenzene, N,N'-methylenebisacrylamide, N,N'-ethylenebisacrylamide, N,N'-1,4-phenylbisacrylamide or 1,4-diacryloylpiperazine.

Said initiator is azo free radical initiator, peroxide free radical initiator, or redox initiator.

Said small chain transfer agent is dithioester or trithiocarbonate organic compound.

Said macromolecular chain transfer agent is selected from hydrophilic polymers with a terminal dithioester or trithiocarbonate group, wherein the polymer are polyethylene glycol, poly(N-isopropylacrylamide), poly(2-hydroxyethyl methacrylate), poly((meth)acrylamide), poly(N,N-dimethylacrylamide), or poly(N,N-dimethylaminoethyl methacrylate).

Said solvent is acetonitrile, acetonitrile/toluene, acetonitrile/tetrahydrofuran, acetonitrile/methanol, acetonitrile/ethanol, acetonitrile/propanol, acetonitrile/butanol, acetonitrile/pentanol, methanol, ethanol, propanol, butanol, pentanol, water, methanol/water, ethanol/water, propanol/water, butanol/water, pentanol/water, 2-butanone, or liquid paraffin.

Said template molecule is propranolol, vasolan, pentamidine, theophylline, caffeine, morphine, atenolol, paracetamol, ibuprofen, naproxen, sameridinum, pentamidine, verapamil, tramadol, dopamine, methylsameridinum, amobarbital, alfuzosin, zidovudine, stavudine, bupivacaine, mepivacaine, ropivacaine, neurosedyn, lamotrigine, monosulfuron, nicotine, taxol, vitamin B, vitamin B2, ephedrine, phenylalanine aniline, phenytoin, diazepam, clenbuterol, bromoclenbuterol, bisphenol A, p-tert-butylphenol, p-nitrophenol, parachlorophenol, benzopyrene, diphenyl phosphate, metsulfuron methyl, monosulfuron, clenbuterol, 9-ethyl adenine, melamine, quercetin, penicillin, erythrocin, oxytetracycline, chloramphenicol, ochratoxin A, tetracycline, norfloxacin, fluoroquinolone, cefalexin, ciprofloxacin, enrofloxacin, ofloxacin, cefathiamidine, amoxicillin, carbamazepine, oxcarbazepine, trimethoprim, monothiophosphate, dithiophosphate, pyrophosphate, phosphamide, thiophosphoryl amide, N-methycarbamate pesticide, dimethylamino carbamate, triazine, amidine, nereistoxin insecticides, ureas, dithiocarbamate, sulfamic acids, glucosinolates sulfonic acid esters, trichloromethylthio, pirimicarb, imidacloprid, atrazine, ametryn, alachlor, acetochlor, butachlor, metolachlor, prometryn, paraquat, quizalofop-p-ethyl, imazethapyr, fomesafen, clomazone, benazolin, amitraz, diazinon, acephate, deltamethrin, isoproturon, fenuron, linuron, metoxuron, chlortoluron, metobromuron, tebuconazole, 2-methyl-4-chlorophenoxyacetic acid, 2,4-dichlorophenoxyacetic acid (2,4-D), 2,4,5-trichlorophenoxy acetic acid, simazine, propazine, terbuthylazine, estradiol, ethinyl estradiol, 17-β-estradiol, testosterone, testosterone glucoside acid, cortisone acetate, dexamethasone acetate, dermhealth cream, enfu cream, compound ketoconazole cream, compound ketone cream, triamcinolone cream, halcinonide solution, ketoconazole, eloson, hydrocortisone butyrate, sicorten, sicorten plus, clobetasol propionate, sokhan, iprobenfos, dexamethasone sodium phosphate, cortisone, hydrocortisone, hydrocortisone acetate, hydrocortisone butyrate, dexamethasone, dexamethasone acetate, prednisone, double beclomethasone propionate, mometasone furoate, fluocinolone acetonide, betamethasone dipropionate, halometasone monohydrate, beclomethasone, betamethasone 21-acetate, prednisolone, tobradex, fluorometholone, triamcinolone, halcinonide, or clobetasol propionate.

In the first aspect, the present invention relates to MIP nanoparticles with surface-grafted hydrophilic polymer brushes, wherein said MIP nanoparticles have a crosslinking degree exceeding 50% and a particle diameter of 10~500 nm, preferably 10~300 nm, and more preferably 10~250 nm, said MIP nanoparticles are capable of recognizing template molecules in biological samples, and in particular pure biological samples, and said MIP nanoparticles are obtained by the hydrophilic macromolecular chain transfer agent and optional small chain transfer agent-mediated RAFT precipitation polymerization of the monovinyl functional monomer and cross-linker in the presence of the template.

In the second aspect, the present invention relates to MIP nanoparticles with surface-grafted hydrophilic polymer brushes, wherein said MIP nanoparticles have a core formed by the cross-linked polymer networks and hydrophilic polymer brushes grafted onto the core, said core has a crosslinking degree exceeding 50% and a particle diameter of 10~500 nm, preferably 10~300 nm, and more preferably 10~250 nm, the core of said MIP nanoparticles has molecularly imprinted cavities capable of recognizing template molecules in biological samples, and in particular pure biological samples.

In one preferred embodiment according to the present invention, said nanoparticles have narrow particle size distribution. The particle size distribution indices determined by dynamic laser scattering according to ISO 13321 are preferably less than or equal to 0.6, preferably less than or equal to 0.5, preferably less than or equal to 0.4, preferably less than or equal to 0.3, preferably less than or equal to 0.2, and preferably less than or equal to 0.1.

In another preferred embodiment according to the present invention, said RAFT precipitation polymerization for the preparation of MIP nanoparticles is induced by the combined use of a hydrophilic macromolecular chain transfer agent and a small chain transfer agent.

In another preferred embodiment according to the present invention, said template molecule is selected from amino acid, biological receptor, nucleic acid, steroid, immunosuppressant, hormone, heparin, antibiotics, vitamin, small pathological and disease biomarker, toxin, pesticide, herbicide, explosive, neurotoxin, endocrine disrupter, nucleotide, nucleoside, oligomeric nucleotide, metabolin, secondary metabolite, drug metabolite, drug, drug intermediate, or pharmic organic molecule. Particularly, said template molecule is selected from propranolol, vasolan, pentamidine, theophylline, caffeine, morphine, atenolol, paracetamol, ibuprofen, naproxen, sameridinum, pentamidine, verapamil, tramadol, dopamine, methylsameridinum, amobarbital, alfuzosin, zidovudine, stavudine, bupivacaine, mepivacaine, ropivacaine, neurosedyn, lamotrigine, monosulfuron, nicotine, taxol, vitamin B, vitamin B2, ephedrine, phenylalanine aniline, phenytoin, diazepam, clenbuterol, bromoclenbuterol, bisphenol A, p-tert-butylphenol, p-nitrophenol, parachlorophenol, benzopyrene, diphenyl phosphate, metsulfuron methyl, monosulfuron, clenbuterol, 9-ethyl adenine, melamine, quercetin, penicillin, erythrocin, tetracycline, oxytetracycline, chloramphenicol, ochratoxin A, norfloxacin, fluoroquinolone, cefalexin, ciprofloxacin, enrofloxacin, ofloxacin, cefathiamidine, amoxicillin, carbamazepine, oxcarbazepine, trimethoprim, monothiophosphate, dithiophosphate, pyrophosphate, phosphamide, thiophosphoryl amide, N-methycarbamate pesticide, dimethylamino carbamate, triazine, amidine, nereistoxin insecticides, ureas, dithiocarbamate, sulfamic acid class, glucosinolates sulfonic acid esters, trichloromethylthio, pirimicarb, imidacloprid, atrazine, ametryn, alachlor, acetochlor, butachlor, metolachlor, prometryn, paraquat, quizalofop-p-ethyl, imazethapyr, fomesafen, clomazone, benazolin, amitraz, diazinon, acephate, deltamethrin, isoproturon, fenuron, linuron, metoxuron, chlortoluron, metobromuron, tebuconazole, 2-methyl-4-chlorophenoxyacetic acid, 2,4-dichlorophenoxyacetic acid (2,4-D), 2,4,5-trichlorophenoxy acetic acid, simazine, propazine, terbuthylazine, estradiol, ethinyl estradiol, 17-β-estradiol, testosterone, testosterone glucoside acid, cortisone acetate, dexamethasone acetate, derm-health cream, enfu cream, compound ketoconazole cream, compound ketone cream, triamcinolone cream, halcinonide solution, ketoconazole, eloson, hydrocortisone butyrate, sicorten, sicorten plus, clobetasol propionate, sokhan, iprobenfos, dexamethasone sodium phosphate, cortisone, hydrocortisone hydrocortisone acetate, hydrocortisone butyrate, dexamethasone, dexamethasone acetate, prednisone, double beclomethasone propionate, mometasone furoate, fluocinolone acetonide, betamethasone dipropionate, halometasone monohydrate, beclomethasone, betamethasone 21-acetate, prednisolone, tobradex, fluorometholone, triamcinolone, halcinonide or clobetasol propionate, preferably propranolol, theophylline, caffeine, bisphenol A, penicillin, erythrocin, tetracycline, norfloxacin, amitraz, diazinon, acephate, bromine cyanate este, 2,4-dichlorophenoxyacetic acid (2,4-D), estradiol or testosterone, and more preferably propranolol or 2,4-dichlorophenoxyacetic acid (2,4-D).

In another preferred embodiment according to the present invention, said monovinyl functional monomer is selected from $C_2$-$C_8$ monoolefin, aromatic vinyl compounds, heterocyclic aromatic vinyl compounds, monoolefin type unsaturated carboxylic acid, carboxylate, ester and amide, vinyl alcohol and its ester, allyl alcohol and its ester, vinyl ether, vinyl lactam, vinyl halide, 1,1-dihaloethylene, (meth)acrylic acid and its ester, salt, and amide, vinylpyridine compound and their combinations, preferably 4-vinylpyridine, 2-vinylpyridine, 4-vinylbenzoic acid, (meth)acrylic acid, trifluoromethylacrylic acid, 2-hydroxyethyl methacrylate, dimethylaminoethyl methacrylate, (meth)acrylamide, 2-acrylamido-2-methylpropanesulfonic acid, 4-vinylimidazole, itaconic acid or N-vinylpyrrolidone or their mixture, and more preferably 4-vinylpyridine or methacrylic acid.

In another preferred embodiment according to the present invention, said crosslinker is a monomer with two or more nonconjugated unsaturated double bond, preferably diol or polyol acrylate, methacrylate, allyl ether, or vinyl ether; the esters obtained from unsaturated monohydric alcohol and vinyl-containing $C_3$-$C_6$ carboxylic acid; the esters obtained from unsaturated carboxylic acid and polyol; linear or branched or cyclic aliphatic or aromatic alkanes with at least two double bond, and said double bond is nonconjugated in case of aliphatic alkane; diamine or polyamine acrylamide, methacrylamide, and N-allyl amine; and their combinations, more preferably ethylene glycol dimethacrylate, trimethylolpropane trimethacrylate, pentaerythritol triacrylate, divinylbenzene, N,N'-methylenebisacrylamide, N,N'-ethylenebisacrylamide, N,N'-phenylbisacrylamide or 1,4- diacryloylpiperazine or their mixture, and more preferably ethylene glycol dimethacrylate.

In another preferred embodiment according to the present invention, said hydrophilic macromolecular chain transfer agent is selected from hydrophilic polymers with a terminal dithioester or trithiocarbonate group, said hydrophilic macromolecular chain transfer agent is preferably polyalcohol, polylactam, polyurethane, poly(meth)acrylic acid, polyacrylamide, polyvinyl alcohol, polyvinyl ether, polyester, polyvinylamine, polyethyleneimine, polyalkylene oxide, poly(carboxylic acid), polyamide, polyanhydride, polyphosphazenes, cellulose, heparin, dextran, polypeptide, fiber protein and elastin, polysaccharide, hyaluronic acid, alginate, gelatin and chitosan gel, albumin, oligopeptides, short chain peptide and oligonucleotides as well as the copolymers synthesized by the monomers of the above polymers, more preferably polyethylene glycol, poly(N-isopropylacrylamide), poly(2-hydroxyethyl methacrylate), polymethacrylamide, poly(N,N-dimethylacrylamide), poly[2-(N,N-dimethyl amino)ethyl methacrylate], poly(N,N-dimethyl aminoethyl methacrylate), poly[[2-(methacryloyloxy)ethyl]dimethyl-(3-sulfopropyl)ammonium hydroxide], poly[N,N-dimethyl-N-methacryloyloxyethyl-N-(3-sulfopropyl)ammonium], poly(2-methacryloyloxyethyl phosphorylcholine), poly[oxygen(11(3-sulfonylpropyltrimethyl-glycidyl)undecyloxy thiolmethyl)ethylene-co-oxygen(1-dodecanethiolmethyl)ethylene], poly(acrylamide-2-methylpropanesulfonic acid), poly(methacryloxyethyl sulfobetaine), poly[[2-(methacryloyloxy)ethyl]trimethyl ammonium chloride], poly(3-sulfopropyl methacrylate potassium salt), poly[4-(dimethyl(2'-methacryloyloxyethyl)amine)butyrate], poly(methacryloxymethyl sulfobetaine), poly(methacrylamide sulfobetaine), poly(styrene sulfonate), poly(styrene sulfonic acid), poly(acrylic acid), poly(methylacrylic acid), sodium polymethacrylate, poly[methoxy tri(ethylene glycol)methacrylate-co-methacrylic acid], polyethylene glycol, poly[methoxy(ethylene glycol)methacrylate], polyalkylene oxide, polyoxyethylene, poly[methoxyoligo(ethylene glycol)methacrylate], poly(hydroxyethyl methacrylate), poly(N-methylglycine), poly(L-glutamic acid), poly(L-lysine), poly(N-isopropyl methacrylamide), poly(N-hydroxymethyl acrylamide), poly[N-(2,2-dimethyl-1,3-dioxolane-methyl)acrylamide], poly[N-(2-hydroxypropyl)methacrylamide], poly(2-hydroxyethyl acrylate), poly(2,3-dihydroxypropyl methacrylate), poly(ether amine), poly(N-vinylpyrrolidone), poly(N-vinylcaprolactam), poly(-oxazoline) and its derivatives, poly[(2-(diethylamino)ethyl acrylate], poly[(2-(dimethylamino)ethyl methylacrylate], poly[(2-(diethylamino)ethyl methylacrylate], poly(-vinylpyridine), poly(l-vinylimidazole), poly(N-acryloylmorpholine), poly(ethylene glycol ethyl phosphate), and copolymers obtained from the monomers of the above polymers.

In another preferred embodiment according to the present invention, said small chain transfer agent has the following structure:

wherein R=alkyl, alkenyl (alkynyl), aryl, aralkyl, substituted alkyl, substituted aryl, carbocyclic or heterocyclic, alkyloxy or dialkylamine;

Z=alkyl, aryl, aralkyl, substituted alkyl, substituted aryl, carbocyclic or heterocyclic, alkylthiol, arylthiol, alkoxycarbonyl, aralkoxycarbonyl, acyloxy, carbamoyl, cyano, N-alkyl, N-aryl-substituted amino, alkoxy, aryloxy, dialkyl or diaryl phosphate, dialkyl or diaryl phosphinic, said small chain transfer agent is selected from dithioester or trithiocarbonate organic compounds and thiocarbonylthio compounds, for example: 1-pyrrole carbothioic acid 2-cyano-2-propyl ester, 1-pyrrole carbothioic acid 2-cyano-2-butyl ester, 1-imidazole carbothioic acid benzyl ester, cumyl dithiobenzoate, cyanoisopropyl dithiobenzoate, 1-carboxyl isobutyl dithiobenzoate, S-1-dodecyl-S'-($\alpha,\alpha$"-dimethyl-$\alpha$"-acetic acid)trithiocarbonate, dodecyl-S"-isopropanoic acid-trithiocarbonate, xanthate derivatives such as O-ethyl S-(1-phenylethyl)dithiocarbonate, O-ethyl S-(2-ethyloxycarbonyl-2-propyl)dithiocarbonate, and O-ethyl S-(2-cyanoisopropyl)dithiocarbonate.

In another preferred embodiment according to the present invention, the molar ratio of the template, monovinyl functional monomer, and crosslinker is 1:1~10:4~80, preferably 1:1~9:4~70, more preferably 1:1~8:4~50, more preferably 1:1~6:4~10, and more preferably 1:1~4:4~10.

In another preferred embodiment according to the present invention, the molar ratio of the total amount of the monovinyl functional monomer and crosslinker to that of the chain transfer agent (including optional small chain transfer agent and hydrophilic macromolecular chain transfer agent) is 500:1~10:1, preferably 200:1~10:1, preferably 150:1~50:1, and more preferably 150:1~80:1.

In another preferred embodiment according to the present invention, the molar percentage of the small chain transfer agent in the total amount of all chain transfer agents including both small chain transfer agent and hydrophilic macromolecular chain transfer agent is 0~95%, preferably 1~85%, more preferably 10~75%, more preferably 15~70%, and more preferably 20~60%.

In another preferred embodiment according to the present invention, said hydrophilic polymer brushes are formed by the macromolecular chain transfer agent.

In another preferred embodiment according to the present invention, the number-average molecular weights of said hydrophilic macromolecular chain transfer agent range from 500 to 50000, preferably from 1000 to 30000, more preferably from 1500 to 8000, and more preferably from 2000 to 5000.

In the third aspect, the present invention relates to a method for preparing the MIP nanoparticles with surface-grafted hydrophilic polymer brushes according to the present invention, which includes the following steps:

1) homogeneously mixing template, monovinyl functional monomer, crosslinker, solvent, free radical initiator, hydrophilic macromolecular chain transfer agent, and optional small chain transfer agent, degassing to remove oxygen and carrying out polymerization at a temperature of 25~100° C., preferably 30~90° C., more preferably 40~80° C., and more preferably 50~70° C., for a period of 1~500 h, preferably 2~200 h, and more preferably 3~100 h, to produce the polymer nanoparticles with entrapped template molecules; and 2) washing the resulting polymer nanoparticles with entrapped template molecules with an appropriate solvent until no template molecules can be detected in the washing solution, so as to obtain the MIP nanoparticles with surface-grafted hydrophilic polymer brushes.

In the fourth aspect, the present invention relates to a method for preparing the MIP nanoparticles with surface-grafted hydrophilic polymer brushes according to the present invention, which includes the following steps:

1) homogeneously mixing template, monovinyl functional monomer, crosslinker, solvent, free radical initiator, hydrophilic macromolecular chain transfer agent, and optional small chain transfer agent, purging with argon or nitrogen for 5~60 min to remove oxygen, polymerizing in an oil bath with a temperature of 25~100° C. for 1~100 h, dispersing with ultrasonic for 5~30 min, and centrifugating with high speed to obtain polymer nanoparticles with entrapped template molecules; and 2) washing the resulting polymer nanoparticles with entrapped template molecules with methanol/acetic acid (with a volume ratio of 10/0.1~10/10) for 12~72 h and methanol for 12~48 h successively until no template molecules can be detected in the washing solution, and drying at 20~60° C. under vacuum to the constant weight, so as to obtain MIP nanoparticles with surface-grafted hydrophilic polymer brushes.

In one preferred embodiment according to the preparation method of the present invention, a series of MIP nanoparticles with surface-grafted hydrophilic polymer brushes and molecular recognition ability toward different template molecules can be prepared by changing the types and used amounts of the functional monomer, crosslinker, initiator, small chain transfer agent, macromolecular chain transfer agent, template, and solvent.

In another preferred embodiment according to the preparation method of the present invention, said initiator is azo type free radical initiator, peroxide type free radical initiator, or redox type initiator, said azo type free radical initiator is preferably selected from 2,2'-azobisisobutyronitrile, 2,2'-azobisisoheptonitrile, 2,2'-azobis(2-cyano-2-butane), 2,2'-azobis (methyl isobutyrate), 4,4'-azobis(4-cyanovaleric acid), 4,4'-azobis(4-cyano-1-pentanol), 1,1'-azobis(cyanocyclohexane), 2-tert-butylazo-2-cyanopropane, 2,2'-azobis{2-methyl-N-[1,1-bis(hydroxymethyl)-2-hydroxyethyl]propionamide}, 2,2'-azobis[(2-methyl-N-hydroxyethyl)propionamide], bihydrochloride 2,2'-azobis(N,N'-bimethylene isobutyl amy), bihydrochloride 2,2'-azobis(2-amidinopropane), 2,2'-azobis(N,N'-bimethylene isobutylamine), 2,2'-azobis{2-methyl-N-[1,1-bis(hydroxymethyl)-2-hydroxyethyl]propionamide}, 2,2'-azobis{2-methyl-N-[1,1-bis(hydroxymethyl)ethyl]propionamide}, 2,2'-azobis[2-methyl-N-(2-hydroxyethyl)propionamide], dihydrate 2,2'-azobis(isobutyramide), 2,2'-azobis(2,2,4-trimethylpentane), 2,2'-azobis(2-methylpropane); said peroxide type free radical initiator is preferably selected from tert-butyl peroxyacetate, tert-butyl peroxybenzoate, tert-butyl peroxy-2-ethylhexanoate, tert-butyl peroxyneodecanoate, tert-butyl perisobutyrate, tert-amyl perpivalate, tert-butyl peroxypivalate, diisopropyl peroxydicarbonate, dicyclohexyl peroxydicarbonate, dicumyl peroxide, benzoyl peroxide, dilauroyl peroxide, potassium persulfate, ammonium persulfate, di-tert-butyl hyponitrite, di-t-butyl peroxide or p-dipropylbenzene hyponitrite, cumyl hydroperoxide, tert-butyl hydroperoxide; for said redox type free radical initiator, wherein the oxidants include organic (alkyl-, aryl-, acyl-)hydrogen peroxide, persulfate, superphosphate, organic peroxide, preferred oxidants include persulfate and organic hydrogen peroxide, and the most preferred oxidants include ammonium, sodium, or potassium persulfate, tert-butyl hydroperoxide, reducing agents include sodium formaldehyde sulfoxylate, sodium sulfite, sodium metabisulfite, sodium dithionite, ascorbic acid, D-isoascorbic acid, hydrazine, hydroxylamine or its salt, reducing sugar, mercaptan, and sulfonic acid derivatives, aluminumtriethyl, triethylborane, tertiary amine, preferred reducing agents include sodium formaldehyde sulfoxylate, sodium metabisulfite, D-isoascorbic acid, sodium hydrosulfite, sodium thiosulfate, sodium sulfite, and the most preferred reducing agent is sodium dithionite.

In another preferred embodiment according to the preparation method of the present invention, the polymerization solvent is acetonitrile, acetonitrile/toluene, acetonitrile/tetrahydrofuran, acetonitrile/methanol, acetonitrile/ethanol, acetonitrile/propanol, acetonitrile/butanol, acetonitrile/pentanol, methanol, ethanol, propanol, butanol, pentanol, water, methanol/water, ethanol/water, propanol/water, butanol/water, pentanol/water, toluene, tetrahydrofuran, N,N-dimethylformamide, dimethyl sulfoxide, 2-butanone or liquid paraffin.

In another preferred embodiment according to the preparation method of the present invention, said RAFT precipitation polymerization is induced by the combined use of both hydrophilic macromolecular chain transfer agent and small chain transfer agent.

In another preferred embodiment according to the preparation method of the present invention, the used amount of said solvent, template, monovinyl functional monomer, crosslinker, initiator, optional small chain transfer agent and hydrophilic macromolecular chain transfer agent is as follows:

1) the molar ratio of the template to monovinyl functional monomer to crosslinker is 1:1~10:4~80, preferably 1:1~9:4~70, more preferably 1:1~8:4~50, more preferably 1:1~6:4~10, and more preferably 1:1~4:4~10, the volume percentage of the monovinyl functional monomer and crosslinker in the whole reaction system is 0.5~10%;

2) the amount of the used initiator is 0.5~10% relative to the total amount of the monovinyl functional monomer and crosslinker, and the molar ratio of the initiator to chain transfer agent (including optional small chain transfer agent and hydrophilic macromolecular chain transfer agent) is 1:1~20;

3) the molar percentage of the small chain transfer agent is 0~95% relative to the total amount of the used chain transfer agent including small chain transfer agent and hydrophilic macromolecular chain transfer agent, preferably 1~85%, more preferably 10~75%, more preferably 15~75%, and more preferably 20~60%.

In the fifth aspect, the present invention relates to the use of the MIP nanoparticles with surface-grafted hydrophilic polymer brushes according to the present invention or obtained by the method described in this invention in the analyses of biological samples, medical clinical diagnostics, foodstuff and environmental monitoring, and/or fabrication of biomimetic sensors.

In the sixth aspect, the present invention relates to a kit, which contains the MIP nanoparticles with surface-grafted hydrophilic polymer brushes according to the present invention or obtained by the method described in this invention.

In the seventh aspect, the present invention relates to a sensor applicable for biological samples, which contains the MIP nanoparticles with surface-grafted hydrophilic polymer brushes according to the present invention or obtained by the method described in this invention.

BRIEF DESCRIPTION OF THE DRAWINGS

In order to further clarify the above-mentioned and other advantages and characteristics of the present invention, a more detailed description of the present invention will be provided by referring to the specific embodiment described in the Figures. It should be noted that these Figures only describe the illustrative embodiment of the present invention, and they should not be considered to limit the scope of the invention. The present invention will be described and explained in a more specific and detailed way by using the following Figures, wherein.

DETAILED DESCRIPTION

Definition

As used in the present invention the term "pure biological samples" denotes the samples that are rich in biological matrices such as proteins (e.g., serum, milk, and urine, etc.).

The term "biological samples" includes many types of samples obtained from the subjects and useful in the present invention. The biological samples may include, but not limited to, solid tissue samples, liquid tissue samples, biological fluids, aspirates, cells, and cell fragments. The specific examples of biological samples include, but not limited to, solid tissue samples, pathological samples, archived samples, biopsy samples, or tissue cultures obtained by remove operation or the cells and cell offsprings obtained from them as well as any section or smear prepared from the above sources. The non-restrictive examples of biological samples include those samples obtained from breast tissue, lymph nodes, and breast cancer. The biological samples also include any material obtained from the vertebrate body, include but not limited to blood, cerebrospinal fluid, serum, plasma, urine, nipple aspirate, fine needle aspiration, tissue lavage fluid such as ductal lavage fluid, saliva, phlegm, ascitic fluid, liver, kidney, breast, bone, marrow, orchis, brain, oarium, skin, lung, prostate, gland, pancreas, uterine neck, stomach, intestines, colon and rectum, bladder, nostril, uterus, semen, lymph, vaginal mixture, synovia, spinal fluid, head and neck, nasopharyngeal neoplasms, amniotic fluid, breast milk, pulmonary or pulmonary surfactant, urine, excrement and liquid samples of biological origin.

As used in the present invention the term "MIP nanoparticles" denotes the polymers containing at least some fractions of cavities (or gaps) complementary with one or more templates with their diameters ranging from 10 to several hundreds of nanometers, wherein the template molecules are added into the monomer solutions containing the crosslinker prior to the polymerization. The resulting polymers have many cavities complementary with the template molecules.

As used in the present invention the term "RAFT precipitation polymerization" is one type of controlled/"living" radical polymerizations. Dithioester or trithiocarbonate derivatives are normally added into a RAFT polymerization system to act as chain transfer agent, which can react with the propagating chain radical to form dormant intermediate during the polymerization process, thus suppressing the irreversible termination side reactions between the propagating chain radicals, and leading to well-controlled polymerization. Self-fragmentation of such dormant intermediate can give rise to a new radical from the corresponding sulfur atom, which is able to reinitiate the monomer to form propagating chain. Since the rates of both the addition or fragmentation processes are much faster than the chain propagation process, which allows the dithioester or trithiocarbonate derivative to quickly transfer between the reactive radicals and dormant species, thus resulting in narrow molecular-mass distribution and controlled/"living" polymerization.

As used in the present invention the term "particle size distribution" denotes the percentages of particles with different diameters in a group of particles, also named as dispersion degree of the particles.

As used in the present invention the term "crosslinking degree" denotes the ratio of the amount of the incorporated crosslinker in the polymer to that of the incorporated crosslinker and functional monomer. The crosslinking degrees of the MIP nanoparticles with surface-grafted hydrophilic polymer brushes obtained according to the present invention are determined by using ASTM D 2765. The crosslinking degree of the MIP obtained according to the present invention is larger than 50%, preferably larger than 60%, more preferably larger than 70%, and more preferably larger than 80%.

EXAMPLES

The following examples are only used to illustrate the embodiments of the present invention, and they should not be interpreted as the limitation of the invention in any way.

Preparation Examples

Example 1

2,4-D (0.83 mmol) is added into a one-neck round-bottom flask (100 mL) containing a mixture of methanol and water (4:1 v/v, 60 mL), and a clear solution is obtained after magnetic stirring, and then 4-vinylpyridine (0.83 mmol) is added into the above solution. After their thorough mixing for 0.5 h, ethylene glycol dimethacrylate (2.50 mmol), small chain transfer agent cumyl dithiobenzoate (CDB) (0.055 mmol), poly(2-hydroxyethyl methacrylate) macromolecular chain transfer agent ($M_{n,NMR}$=4800) (0.034 mmol), and azobisisobutyronitrile (AIBN) (0.028 mmol) are added successively. After being purged with argon for 30 min, the reaction mixture is sealed and immersed into a thermostatted oil bath at 60° C. The polymerization is allowed to take place for 10 h. The resulting polymer particles are collected by high speed centrifugation.

The above product is purified by being washed with methanol/acetic acid (9:1 v/v) and methanol until no template is detectable in the centrifugated supernatant. After being dried at 40° C. under vacuum for 48 h, MIP nanoparticles with surface-grafted poly(2-hydroxyethyl methacrylate) brushes ($M_{n,NMR}$=4800) are obtained. Said MIP nanoparticles have a diameter of 111 nm (DLS, with methanol as the solvent, the same below) and a crosslinking degree of 75%.

The non-imprinted nanoparticles with surface-grafted poly(2-hydroxyethyl methacrylate) brushes ($M_{n,NMR}$=4800) are synthesized and purified under the identical conditions except that the template is omitted.

Example 2

2,4-D (0.83 mmol) is added into a one-neck round-bottom flask (100 mL) containing a mixture of methanol and water (4:1 v/v, 60 mL), and a clear solution is obtained after magnetic stirring, and then 4-vinylpyridine (0.83 mmol) is added into the above solution. After their thorough mixing for 0.5 h, ethylene glycol dimethacrylate (2.50 mmol), small chain transfer agent cumyl dithiobenzoate (CDB) (0.055 mmol), poly(2-hydroxyethyl methacrylate) macromolecular chain transfer agent ($M_{n,NMR}$=3250) (0.034 mmol), and azobisisobutyronitrile (AIBN) (0.028 mmol) are added successively. After being purged with argon for 30 min, the reaction mixture is sealed and immersed into a thermostatted oil bath at 60° C. The polymerization is allowed to take place for 10 h. The resulting polymer particles are collected by high speed centrifugation.

The above product is purified by being washed with methanol/acetic acid (9:1 v/v) and methanol until no template is detectable in the centrifugated supernatant. After being dried at 40° C. under vacuum for 48 h, MIP nanoparticles with surface-grafted poly(2-hydroxyethyl methacrylate) brushes ($M_{n,NMR}$=3250) are obtained. Said MIP nanoparticles have a diameter of 147 nm and a crosslinking degree of 75%.

The non-imprinted nanoparticles with surface-grafted poly(2-hydroxyethyl methacrylate) brushes ($M_{n,NMR}$=3250) are synthesized and purified under the identical conditions except that the template is omitted.

Example 3

Propranolol (0.83 mmol) is added into a one-neck round-bottom flask (100 mL) containing a mixture of acetonitrile and methanol (1:1 v/v, 60 mL), and a clear solution is obtained after magnetic stirring, and then methacrylic acid (0.83 mmol) is added into the above solution. After their thorough mixing for 0.5 h, ethylene glycol dimethacrylate (2.50 mmol), small chain transfer agent cumyl dithiobenzoate (CDB) (0.055 mmol), poly(2-hydroxyethyl methacrylate) macromolecular chain transfer agent ($M_{n,NMR}$=4800) (0.034 mmol), and azobisisobutyronitrile (AIBN) (0.028 mmol) are added successively. After being purged with argon for 30 min, the reaction mixture is sealed and immersed into a thermostatted oil bath at 60° C. The polymerization is allowed to take place for 24 h. The resulting polymer particles are collected by high speed centrifugation.

The above product is purified by being washed with methanol/acetic acid (9:1 v/v) and methanol until no template is detectable in the centrifugated supernatant. After being dried at 40° C. under vacuum for 48 h, MIP nanoparticles with surface-grafted poly(2-hydroxyethyl methacrylate) brushes ($M_{n,NMR}$=4800) (propranolol-MIP-1) are obtained. Said MIP nanoparticles have a diameter of 220 nm and a crosslinking degree of 75%.

The non-imprinted nanoparticles with surface-grafted poly(2-hydroxyethyl methacrylate) brushes ($M_{n,NMR}$=4800) (propranolol-CP-1) are synthesized and purified under the identical conditions except that the template is omitted.

Example 4

Propranolol (0.83 mmol) is added into a one-neck round-bottom flask (100 mL) containing a mixture of acetonitrile and methanol (2:1 v/v, 60 mL), and a clear solution is obtained after magnetic stirring, and then methacrylic acid (0.83 mmol) is added into the above solution. After their thorough mixing for 0.5 h, ethylene glycol dimethacrylate (2.50 mmol), small chain transfer agent cumyl dithiobenzoate (CDB) (0.055 mmol), poly(2-hydroxyethyl methacrylate) macromolecular chain transfer agent ($M_{n,NMR}$=4800) (0.034 mmol), and azobisisobutyronitrile (AIBN) (0.028 mmol) are added successively. After being purged with argon for 30 min, the reaction mixture is sealed and immersed into a thermostatted oil bath at 60° C. The polymerization is allowed to take place for 16 h. The resulting polymer particles are collected by high speed centrifugation.

The above product is purified by being washed with methanol/acetic acid (9:1 v/v) and methanol until no template is detectable in the centrifugated supernatant. After being dried at 40° C. under vacuum for 48 h, MIP nanoparticles with surface-grafted poly(2-hydroxyethyl methacrylate) brushes (i.e., propranolol-MIP-2) are obtained. Said MIP nanoparticles have a diameter of 182 nm and a crosslinking degree of 75%.

The non-imprinted nanoparticles with surface-grafted poly(2-hydroxyethyl methacrylate) brushes (propranolol-CP-2) are synthesized and purified under the identical conditions except that the template is omitted.

Example 5

2,4-D (0.83 mmol) is added into a one-neck round-bottom flask (100 mL) containing a mixture of methanol and water (4:1 v/v, 60 mL), and a clear solution is obtained after magnetic stirring, and then 4-vinylpyridine (0.83 mmol) is added into the above solution. After their thorough mixing for 0.5 h, ethylene glycol dimethacrylate (3.32 mmol), small chain transfer agent cumyl dithiobenzoate (CDB) (0.055 mmol), poly(2-hydroxyethyl methacrylate) macromolecular chain transfer agent ($M_{n,NMR}$=4800) (0.034 mmol), and azobisisobutyronitrile (AIBN) (0.028 mmol) are added successively. After being purged with argon for 30 min, the reaction mixture is sealed and immersed into a thermostatted oil bath at 60° C. The polymerization is allowed to take place for 10 h. The resulting polymer particles are collected by high speed centrifugation.

The above product is purified by being washed with methanol/acetic acid (9:1 v/v) and methanol until no template is detectable in the centrifugated supernatant. After being dried at 40° C. under vacuum for 48 h, MIP nanoparticles with surface-grafted poly(2-hydroxyethyl methacrylate) brushes ($M_{n,NMR}$=4800) are obtained. Said MIP nanoparticles have a diameter of 180 nm and a crosslinking degree of 80%.

Example 6

The MIP nanoparticles with surface-grafted hydrophilic polymer brushes according to the present invention are prepared in the same way as example 5 except that the molar ratio of the template to functional monomer is 1:10. Said MIP nanoparticles have a diameter of 215 nm and a crosslinking degree of 80%.

Example 7

The MIP nanoparticles with surface-grafted hydrophilic polymer brushes according to the present invention are prepared in the same way as example 5 except that the molar ratio of the template to functional monomer is 1:5. Said MIP nanoparticles have a diameter of 195 nm and a crosslinking degree of 80%.

Example 8

The MIP nanoparticles with surface-grafted hydrophilic polymer brushes according to the present invention are prepared in the same way as example 5 except that the molar ratio of the functional monomer to crosslinker is 1:80. Said MIP nanoparticles have a diameter of 850 nm and a crosslinking degree of 98.8%.

Example 9

The MIP nanoparticles with surface-grafted hydrophilic polymer brushes according to the present invention are prepared in the same way as example 5 except that the molar ratio of the functional monomer to crosslinker is 1:40. Said MIP nanoparticles have a diameter of 480 nm and a crosslinking degree of 97.6%.

Example 10

The MIP nanoparticles with surface-grafted hydrophilic polymer brushes according to the present invention are prepared in the same way as example 5 except that the molar ratio of the functional monomer to crosslinker is 1:20. Said MIP nanoparticles have a diameter of 384 nm and a crosslinking degree of 95.2%.

Example 11

The MIP nanoparticles with surface-grafted hydrophilic polymer brushes according to the present invention are prepared in the same way as example 5 except is that the molar ratio of the functional monomer to crosslinker is 1:60. Said MIP nanoparticles have a diameter of 620 nm and a crosslinking degree of 98.4%.

Example 12

The MIP nanoparticles with surface-grafted hydrophilic polymer brushes according to the present invention are prepared in the same way as example 5 except that the molar ratio of the functional monomer to crosslinker is 0.5:100. Said MIP nanoparticles have a diameter of 240 nm and a crosslinking degree of 80%.

Example 13

The MIP nanoparticles with surface-grafted hydrophilic polymer brushes according to the present invention are prepared in the same way as example 5 except that the molar ratio of the initiator to the functional monomer and crosslinker is 5:100. Said MIP nanoparticles have a diameter of 130 nm and a crosslinking degree of 80%.

Example 14

The MIP nanoparticles with surface-grafted hydrophilic polymer brushes according to the present invention are prepared in the same way as example 5 except that the molar ratio of the initiator to the functional monomer and crosslinker is 10:100. Said MIP nanoparticles have a diameter of 100 nm and a crosslinking degree of 80%.

Example 15

The MIP nanoparticles with surface-grafted hydrophilic polymer brushes according to the present invention are prepared in the same way as example 5 except that only hydrophilic macromolecular chain transfer agent is used in the polymerization system. Said MIP nanoparticles have a diameter of 106 nm and a crosslinking degree of 80%.

Example 16

The MIP nanoparticles with surface-grafted hydrophilic polymer brushes according to the present invention are prepared in the same way as example 5 except that the molar ratio of the initiator to chain transfer agents is 1:1. Said MIP nanoparticles have a diameter of 220 nm and a crosslinking degree of 80%.

Example 17

The MIP nanoparticles with surface-grafted hydrophilic polymer brushes according to the present invention are prepared in the same way as example 5 except that the molar ratio of the initiator to chain transfer agents is 1:20. Said MIP nanoparticles have a diameter of 137 nm and a crosslinking degree of 80%.

Example 18

The MIP nanoparticles with surface-grafted hydrophilic polymer brushes according to the present invention are prepared in the same way as example 5 except that the molar ratio of the initiator to chain transfer agents is 1:10. Said MIP nanoparticles have a diameter of 145 nm and a crosslinking degree of 80%.

Example 19

The MIP nanoparticles with surface-grafted hydrophilic polymer brushes according to the present invention are prepared in the same way as example 5 except that the molar ratio of the initiator to chain transfer agents is 1:5. Said MIP nanoparticles have a diameter of 150 nm and a crosslinking degree of 80%.

Example 20

The MIP nanoparticles with surface-grafted hydrophilic polymer brushes according to the present invention are prepared in the same way as example 5 except that the molar percentage of the small chain transfer agent in the total chain transfer agents is 95%. Said MIP nanoparticles have a diameter of 450 nm and a crosslinking degree of 80%.

Example 21

The MIP nanoparticles with surface-grafted hydrophilic polymer brushes according to the present invention are prepared in the same way as example 5 except that the molar percentage of the small chain transfer agent in the total chain transfer agents is 50%. Said MIP nanoparticles have a diameter of 104 nm and a crosslinking degree of 80%.

Example 22

The MIP nanoparticles with surface-grafted hydrophilic polymer brushes according to the present invention are prepared in the same way as example 5 except that the template is paraquat. Said MIP nanoparticles have a diameter of 169 nm and a crosslinking degree of 80%.

Example 23

The MIP nanoparticles with surface-grafted hydrophilic polymer brushes according to the present invention are prepared in the same way as example 5 except that the functional monomer is itaconic acid. Said MIP nanoparticles have a diameter of 180 nm and a crosslinking degree of 80%.

Example 24

The MIP nanoparticles with surface-grafted hydrophilic polymer brushes according to the present invention are prepared in the same way as example 5 except that the functional monomer is N-vinylpyrrolidone. Said MIP nanoparticles have a diameter of 120 nm and a crosslinking degree of 80%.

Example 25

The MIP nanoparticles with surface-grafted hydrophilic polymer brushes according to the present invention are prepared in the same way as example 5 except that the crosslinker is trimethylolpropane trimethacrylate. Said MIP nanoparticles have a diameter of 208 nm and a crosslinking degree of 80%.

Example 26

The MIP nanoparticles with surface-grafted hydrophilic polymer brushes according to the present invention are prepared in the same way as example 5 except that the crosslinker is divinylbenzene. Said MIP nanoparticles have a diameter of 174 nm and a crosslinking degree of 80%.

Example 27

The MIP nanoparticles with surface-grafted hydrophilic polymer brushes according to the present invention are prepared in the same way as example 5 except that the hydrophilic macromolecular chain transfer agent is polyethylene glycol and the solvent is a mixture of N,N-dimethylformamide and acetonitrile (4:1 v/v). Said MIP nanoparticles have a diameter of 370 nm and a crosslinking degree of 80%.

Example 28

The MIP nanoparticles with surface-grafted hydrophilic polymer brushes according to the present invention are prepared in the same way as example 5 except that the hydrophilic macromolecular chain transfer agent is poly(N-isopropylacrylamide) and the solvent is a mixture of N,N-dimethylformamide and acetonitrile (4:1 v/v). Said MIP nanoparticles have a diameter of 480 nm and a crosslinking degree of 80%.

Example 29

The MIP nanoparticles with surface-grafted hydrophilic polymer brushes according to the present invention are prepared in the same way as example 5 except that the small chain transfer agent is O-ethyl S-(2-ethyloxycarbonyl-2-propyl) dithiocarbonate. Said MIP nanoparticles have a diameter of 500 nm and a crosslinking degree of 80%.

Example 30

The MIP nanoparticles with surface-grafted hydrophilic polymer brushes according to the present invention are prepared in the same way as example 5 except that the solvent is butanone. Said MIP nanoparticles have a diameter of 450 nm and a crosslinking degree of 80%.

Figure 1:
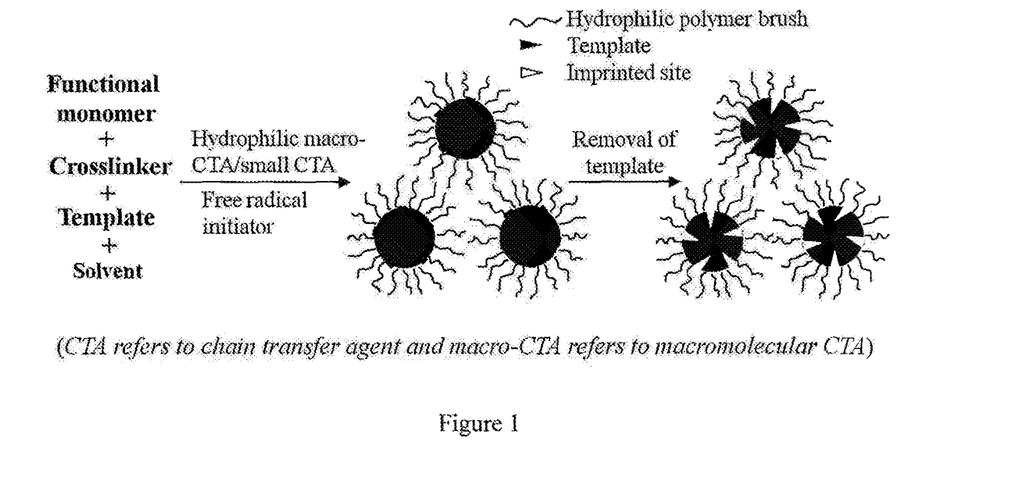
FIG. 1. Schematic illustration of the preparation of MIP nanoparticles with surface-grafted hydrophilic polymer brushes via hydrophilic macromolecular chain transfer agent-mediated RAFT precipitation polymerization.
Figure 2:
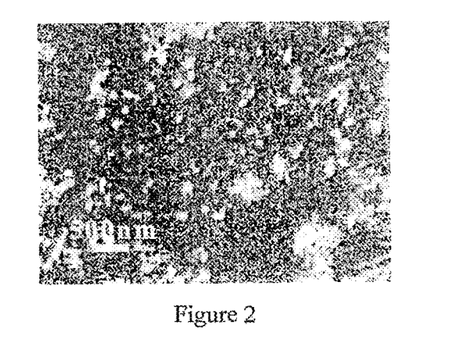
FIG. 2. Scanning electron microscope image of the MIP nanoparticles (with 2,4-D as the template) with surface-grafted hydrophilic poly(2-hydroxyethyl methacrylate) brushes ($M_{n,NMR}$=4800) prepared via hydrophilic macromolecular chain transfer agent-mediated RAFT precipitation polymerization.
Figure 3:
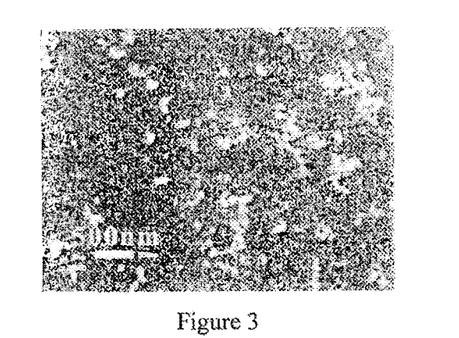
FIG. 3. Scanning electron microscope image of the non-imprinted polymer nanoparticles (corresponding to the MIP in FIG. 2) with surface-grafted hydrophilic poly(2-hydroxyethyl methacrylate) brushes ($M_{n,NMR}$=4800) prepared via hydrophilic macromolecular chain transfer agent-mediated RAFT precipitation polymerization.
Figure 4:
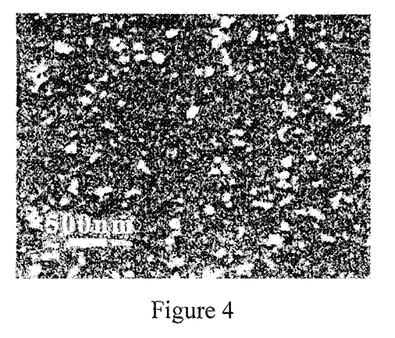
FIG. 4. Scanning electron microscope image of the MIP nanoparticles (with propranolol as the template) (propranolol-MIP-2) with surface-grafted hydrophilic poly(2-hydroxyethyl methacrylate) brushes ($M_{n,NMR}$=4800) prepared via hydrophilic macromolecular chain transfer agent-mediated RAFT precipitation polymerization.
Figure 5:
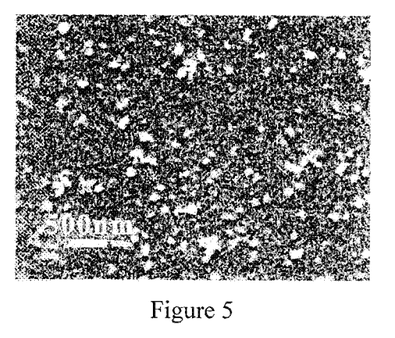
FIG. 5. Scanning electron microscope image of the non-imprinted polymer nanoparticles (corresponding to the MIP in FIG. 4) (propranolol-CP-2) with surface-grafted hydrophilic poly(2-hydroxyethyl methacrylate) brushes ($M_{n,NMR}$=4800) prepared via hydrophilic macromolecular chain transfer agent-mediated RAFT precipitation polymerization.

As illustrated in FIGS. 2, 4, and 5, MIP nanoparticles with surface-grafted hydrophilic polymer brushes are obtained by using the method described in the present invention. Without being bound to any theory, the inventors believe that the active initiating center will transfer to the macromolecular chain transfer agent after the "living" RAFT polymerization is initiated because of the exixtence of the macromolecular chain transfer agent described in the present invention in the beginning of the polymerization, and then in the specific reaction condition, a number of active initiating centers from chain transfer agent will initiate the "living" crosslinking polymerization of the monovinyl functional monomer and crosslinker, leading to nanoparticles and forming hydrophilic polymer brushes outside the cores of nanoparticles by the grafting of the end of the macromolecular chain transfer agent. In addition, the obtained nanoparticles have uniform sizes, i.e., narrow size distribution, because of the "living" nature of RAFT polymerization, as shown in FIGS. 2, 4, and 5. After removal of the template molecules by washing, imprinted cavities of the template molecules will be created in the cores of the nanoparticles, the nanoparticles in the present invention are thus capable of specific bindings toward the template molecules in the samples, i.e., high selective bindings, as demonstrated by the following examples.

Measurement Examples

Figure 6:
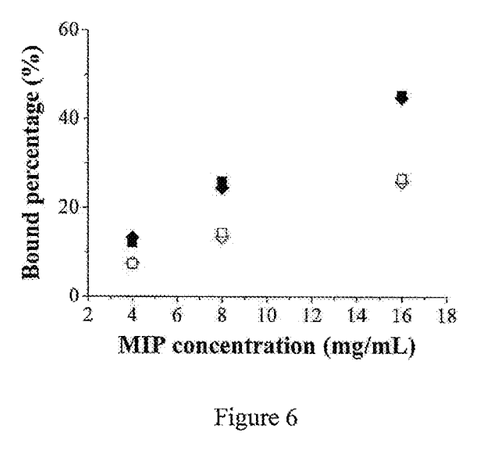
FIG. 6. Equilibrium bindings of 2,4-D to the MIP (with 2,4-D as the template, filled symbols) and non-imprinted polymer (empty symbols) nanoparticles with surface-grafted hydrophilic poly(2-hydroxyethyl methacrylate) brushes ($M_{n,NMR}$=4800) in pure milk (square) and pure bovine serum (diamond) (binding temperature: 25° C., the concentration of 2,4-D: 0.02 mM).

FIG. 6, different amounts of MIP and non-imprinted polymer nanoparticles with surface-grafted poly(2-hydroxyethyl methacrylate) brushes ($M_{n,NMR}$=4800) are added into a 2,4-D solution in pure milk or pure bovine serum (the concentration of 2,4-D: 0.02 mM), and the mixed solutions are incubated at ambient temperature for 16 h. After the solid particles are removed by centrifugation, 400 μL of the supernatants are collected, to which 600 μL of acetonitrile is added. After 5 mM of ultrasonic treatment of the above mixtures, the samples are centrifuged and all the supernatants are collected, to which some acetonitrile/water (3/2 v/v) is added to reach a final volume of 1 mL. The amounts of 2,4-D in the solutions are determined by HPLC, from which the template 2,4-D bound to the MIP and non-imprinted polymer nanoparticles with surface-grafted hydrophilic poly(2-hydroxyethyl methacrylate) brushes ($M_{n,NMR}$=4800) can be derived.

HPLC measurement condition: A mixture of methanol and 0.5% aqueous solution of acetic acid (3/1 v/v for milk sample and 4/1 v/v for bovine serum sample) is utilized as the mobile phase at a flow rate of 1 mL/min. The wavelength used for the determination is 284 nm.

Figure 7:
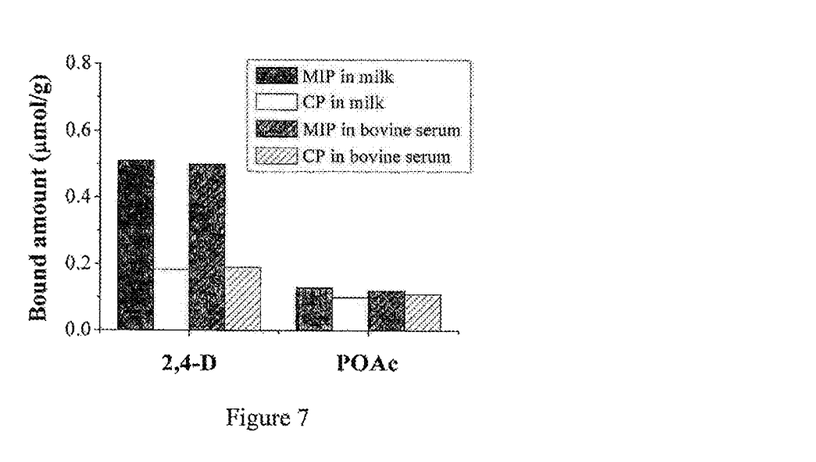
FIG. 7. Selective bindings of the MIP (with 2,4-D as the template) and non-imprinted polymer (CP) nanoparticles with surface-grafted hydrophilic poly(2-hydroxyethyl methacrylate) brushes ($M_{n,NMR}$=4800) toward a mixture of 2,4-D and its analogue phenoxyacetic acid (POAc) in pure milk and pure bovine serum (binding temperature: 25° C., both the concentrations of 2,4-D and POAc are 0.02 mM, and the concentrations of MIP and CP are 12 mg/mL).

FIG. 7, a certain amount of MIP and non-imprinted polymer nanoparticles with surface-grafted poly(2-hydroxyethyl methacrylate) brushes ($M_{n,NMR}$=4800) is added into a mixed solution of 2,4-D and POAc in pure milk and pure bovine serum (both the concentrations of 2,4-D and POAc are 0.02 mM), and the mixed solutions are incubated at ambient temperature for 16 h. After the solid particles are removed by centrifugation, 400 μL of the supernatants are collected, to which 600 μL of acetonitrile is added to precipitate all the proteins in the samples. After 5 min of ultrasonic treatment of the above mixtures, the samples are centrifuged and all the supernatants are collected, to which some acetonitrile/water (3/2 v/v) is added to reach a final volume of 1 mL. The amounts of 2,4-D and POAc in the solutions are determined by HPLC, from which the template 2,4-D and its analogue POAc bound to the MIP and non-imprinted polymer nanoparticles with surface-grafted hydrophilic poly(2-hydroxyethyl methacrylate) brushes ($M_{n,NMR}$=4800) can be derived.

HPLC measurement condition: A mixture of methanol and 0.5% aqueous solution of acetic acid (3/2 v/v) is utilized as the mobile phase at a flow rate of 1 mL/min, and the wavelength used for the determination is 272 nm.

Figure 8:
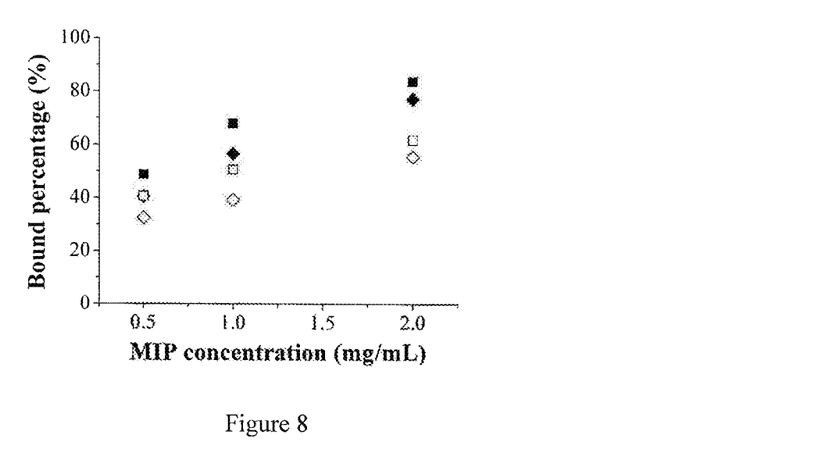
FIG. 8. Equilibrium bindings of propranolol to the MIP (propranolol-MIP-2, filled symbols) and non-imprinted polymer (propranolol-CP-2, empty symbols) nanoparticles with surface-grafted hydrophilic poly(2-hydroxyethyl methacrylate) brushes ($M_{n,NMR}$=4800) in pure milk (square) and pure bovine serum (diamond) (binding temperature: 25° C., the concentration of propranolol: 0.05 mM).

FIG. 8, different amounts of MIP (propranolol-MIP-2) and non-imprinted polymer (CP) nanoparticles with surface-grafted poly(2-hydroxyethyl methacrylate) brushes ($M_{n,NMR}$=4800) are added into a propranolol solution in pure milk or pure bovine serum (the concentration of propranolol: 0.05 mM), and the mixed solutions are incubated at ambient temperature for 16 h. After the solid particles are removed by centrifugation, 400 μL of the supernatants are collected, to which 600 μL of acetonitrile is added. After 5 min of ultrasonic treatment of the above mixtures, the samples are centrifuged and all the supernatants are collected, to which some acetonitrile/water (3/2 v/v) is added to reach a final volume of 1 mL. The amounts of propranolol in the solutions are determined by HPLC, from which the template propranolol bound to the MIP (propranolol-MIP-2) and non-imprinted polymer (CP) nanoparticles with surface-grafted hydrophilic poly(2-hydroxyethyl methacrylate) brushes ($M_{n,NMR}$=4800) can be derived.

HPLC measurement condition: A mixture of acetonitrile and 0.4% aqueous solution of triethylamine (7/3 v/v) is utilized as the mobile phase at a flow rate of 1 mL/min, and the wavelength used for the determination is 293 nm.

Figure 9:
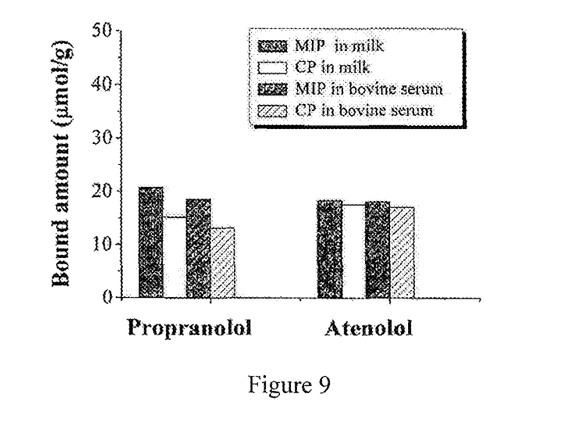
FIG. 9. Selective bindings of the MIP (propranolol-MIP-2) and non-imprinted polymer (CP) (propranolol-CP-2) nanoparticles with surface-grafted hydrophilic poly(2-hydroxyethyl methacrylate) brushes ($M_{n,NMR}$=4800) toward a mixture of propranolol and its analogue atenolol in pure milk and pure bovine serum (binding temperature: 25° C., both the concentrations of propranolol and atenolol are 0.05 mM, the concentrations of propranolol-MIP-2 and propranolol-CP-2 are 2 mg/mL).

FIG. 9, a certain amount of MIP (propranolol-MIP-2) and their non-imprinted polymer (CP) nanoparticles with surface-grafted poly(2-hydroxyethyl methacrylate) brushes ($M_{n,NMR}$=4800) is added into a mixed solution of propranolol and atenolol in pure milk or pure bovine serum (both the concentrations of propranolol and atenolol are 0.05 mM), and the mixed solutions are incubated at ambient temperature for 16 h. After the solid particles are removed by centrifugation, 400 μL of the supernatants are collected, to which 600 μL of acetonitrile is added. After 5 min of ultrasonic treatment of the above mixtures, the samples are centrifuged and all the supernatants are collected, to which some acetonitrile/water (3/2 v/v) is added to reach a final volume of 1 mL. The amounts of propranolol and atenolol in the solutions are determined by HPLC, from which the template propranolol and its analogue atenolol bound to the MIP (propranolol-MIP-2) and non-imprinted polymer (CP) nanoparticles with surface-grafted hydrophilic poly(2-hydroxyethyl methacrylate) brushes ($M_{n,NMR}$=4800) can be derived.

HPLC measurement condition: A mixture of acetonitrile and 0.4% aqueous solution of triethylamine (7/3 v/v) is utilized as the mobile phase at a flow rate of 1 mL/min, and the wavelength used for the determination is 275 nm.

As demonstrated by the above measurement examples, the MIP nanoparticles obtained in the present invention can show specific template binding capability in aqueous samples as well as biological samples, and in particular pure biological samples, as good as what they show in the organic solvent (after considering the inevitable experimental errors). Without being bound to any theory, the applicants believe that the above results are attributed to generation of MIP nanoparticles with specific structures and properties by the method described in the present invention, and such MIP nanoparticles can efficiently recognize the template molecules in aqueous samples as well as biological samples, and in particular pure biological samples, and they are not interfered by the existence of components rich in biological samples such as proteins. This is unknown and unpredictable prior to the present invention. Therefore, the MIP nanoparticles obtained in the present invention can be efficiently used in aqueous samples and biological samples, and in particular pure biological samples, for specifically recognizing the targeted template molecules. For example, the MIP nanoparticles obtained according to the present invention can conveniently recognize the antibiotic and pesticide residues in milk, which is of great potential in food safety area.

On the basis of their above-mentioned characteristics, the MIP nanoparticles obtained in the present invention can be used in analyses of biological samples, medical clinical immunoassays, foodstuff and enviromnental monitoring, and/or fabrication of biomimetic sensors. For example, the MIP nanoparticles obtained in the present invention can be used for the preparation of sensors applicable for biological samples.

Although the present invention has been illustrated by using specific embodiments, many other alterations, modifications and other applications will become obvious to those skilled in the art. Therefore, preferably the present invention is not limited by the specific disclosed content of the above description, but is defined solely by the claims appended hereto.

What is claimed is:

1. A molecularly imprinted polymer nanoparticle with surface-grafted hydrophilic polymer brushes, wherein said nanoparticle has a core formed by the crosslinked polymer networks and hydrophilic polymer brushes on the surfaces of the core, said core has a crosslinking degree exceeding 50% and a particle diameter of 10-500 nm, and the core of said nanoparticle has molecularly imprinted cavities that are capable of recognizing the template molecules in biological samples.

2. The molecularly imprinted polymer nanoparticle according to claim 1, wherein said molecularly imprinted polymer nanoparticle is synthesized by a reversible addition-fragmentation chain transfer (RAFT) precipitation polymerization of monovinyl functional monomer and crosslinker mediated by hydrophilic macromolecular chain transfer agent and optional small molecule chain transfer agent in the presence of template molecule.

3. The molecularly imprinted polymer nanoparticle according to claim 2, wherein said reversible addition-fragmentation chain transfer (RAFT) precipitation polymerization is induced by the combined use of the hydrophilic macromolecular chain transfer agent and the small molecule chain transfer agent.

4. The molecularly imprinted polymer nanoparticle according to claim 2, wherein said template molecule is selected from the group consisting of amino acid, biological receptor, nucleic acid, steroid, immunosuppressant, hormone, heparin, antibiotics, vitamin, small pathological and disease biomarker, toxin, pesticide, herbicide, explosive, neurotoxin, endocrine disrupter, nucleotide, nucleoside, oligomeric nucleotide, metabolin, secondary metabolite, drug metabolite, drug, drug intermediate, and pharmic organic molecule.

5. The molecularly imprinted polymer nanoparticle according to claim 2, wherein said monovinyl functional monomer is selected from the group consisting of $C_2$-$C_8$ monoolefin, aromatic vinyl compounds, heterocyclic aromatic vinyl compounds, monoolefin type unsaturated carboxylic acid, carboxylate, ester and amide, vinyl alcohol and its ester, allyl alcohol and its ester, vinyl ether, vinyl lactam, vinyl halide, 1,1-dihaloethylene, (meth)acrylic acid and its ester, salt, amide, vinylpyridine compound, trifluoromethylacrylic acid and combinations thereof.

6. The molecularly imprinted polymer nanoparticle according to claim 2, wherein said crosslinker is a monomer with two or more nonconjugated unsaturated double bond.

7. The molecularly imprinted polymer nanoparticle according to claim 2, wherein said hydrophilic macromolecular chain transfer agent is hydrophilic polymers with a terminal dithioester or trithiocarbonate group.

8. The molecularly imprinted polymer nanoparticle according to claim 2, wherein said small molecule chain transfer agent has the following structure:

wherein R=alkyl, alkenyl, alkynyl, aryl, aralkyl, substituted alkyl, substituted aryl, carbocyclic or heterocyclic, alkyloxy or dialkylamine; Z=alkyl, aryl, aralkyl, substituted alkyl, substituted aryl, carbocyclic or heterocyclic, alkylthiol, arylthiol, alkoxycarbonyl, aralkoxycarbonyl, acyloxy, carbamoyl, cyano, N-alkyl, N-aryl-substituted amino, alkoxy, aryloxy, dialkyl or diaryl phosphate, dialkyl or diaryl phosphinic.

9. The molecularly imprinted polymer nanoparticle according to claim 2, wherein the molar ratio of the template molecule to monovinyl functional monomer to crosslinker is 1:1-10:4-80.

10. The molecularly imprinted polymer nanoparticle according to claim 2, wherein the molar ratio of the total amount of monovinyl functional monomer and crosslinker to that of the hydrophilic macromolecular chain transfer agent and optional small molecule chain transfer agent is 500:1-10:1.

11. The molecularly imprinted polymer nanoparticle according to claim 2, wherein the molar percentage of the small molecule chain transfer agent in the total amount of both small molecule chain transfer agent and hydrophilic macromolecular chain transfer agent is 0-95%.

12. The molecularly imprinted polymer nanoparticle according to claim 2, wherein the number-average molecular weight of said hydrophilic macromolecular chain transfer agent is in a range from of 500 to 50,000.

13. The molecularly imprinted polymer nanoparticle according to claim 1, wherein said molecularly imprinted polymer nanoparticle has a narrow particle size distribution, and the narrow particle size distribution indices of said nanoparticle determined by dynamic laser scattering according to ISO 13321 is less than or equal to 0.6.

14. The molecularly imprinted polymer nanoparticle according to claim 1, wherein said hydrophilic polymer brushes are formed by the macromolecular chain transfer agent.

15. A kit comprising the molecularly imprinted polymer nanoparticle with surface-grafted hydrophilic polymer brushes according to claim 1.

16. A sensor applicable for biological samples comprising the molecularly imprinted polymer nanoparticle with surface-grafted hydrophilic polymer brushes according to claim 1.

* * * * *